(12) United States Patent
Algotsson et al.

(10) Patent No.: US 10,371,608 B2
(45) Date of Patent: Aug. 6, 2019

(54) SAMPLE PRESERVATION METHOD AND SAMPLE PRESERVATION SUBSTRATE

(71) Applicant: GE HEALTHCARE BIO-SCIENCES AB, Uppsala (SE)

(72) Inventors: Mattias Algotsson, Uppsala (SE); Miles W. Burrows, Cardiff (GB); Jimmy Hedin Dahlstrom, Uppsala (SE); Ylva Laurin, Uppsala (SE); Ronnie Palmgren, Uppsala (SE); Jinyu Zou, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 179 days.

(21) Appl. No.: 14/355,027

(22) PCT Filed: Oct. 29, 2012

(86) PCT No.: PCT/SE2012/051168
§ 371 (c)(1),
(2) Date: Apr. 29, 2014

(87) PCT Pub. No.: WO2013/066249
PCT Pub. Date: May 10, 2013

(65) Prior Publication Data
US 2014/0302521 A1   Oct. 9, 2014

(30) Foreign Application Priority Data

Oct. 31, 2011   (GB) .................................. 1118731.7

(51) Int. Cl.

| | |
|---|---|
| *G01N 1/28* | (2006.01) |
| *B01L 3/00* | (2006.01) |
| *D21H 13/40* | (2006.01) |
| *D21H 17/22* | (2006.01) |
| *D21H 17/52* | (2006.01) |
| *D21H 17/24* | (2006.01) |

(52) U.S. Cl.
CPC .................. *G01N 1/28* (2013.01); *B01L 3/50* (2013.01); *D21H 13/40* (2013.01); *D21H 17/22* (2013.01); *D21H 17/24* (2013.01); *D21H 17/52* (2013.01); *B01L 2300/126* (2013.01)

(58) Field of Classification Search
CPC .......... G01N 1/02; D21H 13/40; D21H 17/22; D21H 17/24; D21H 17/52; B01L 2300/126; B01L 3/508
See application file for complete search history.

(56) References Cited

U.S. PATENT DOCUMENTS

| | | |
|---|---|---|
| 3,070,486 A | 12/1962 | Novak |
| 3,300,474 A | 1/1967 | Flodin |
| 3,645,692 A | 2/1972 | Stork et al. |
| 5,252,489 A * | 10/1993 | Macri .............................. 436/87 |
| 5,567,615 A * | 10/1996 | Degen ................... B01D 29/01 210/691 |
| 5,725,774 A * | 3/1998 | Neyer ................ B01D 39/1623 210/483 |
| 6,309,887 B1 | 10/2001 | Ray |
| 8,328,023 B2 | 12/2012 | Weiss et al. |
| 2010/0209957 A1* | 8/2010 | Hogan et al. .................... 435/29 |

FOREIGN PATENT DOCUMENTS

| | | | |
|---|---|---|---|
| EP | 325413 A2 * | 7/1989 | ............. G01N 33/49 |
| EP | 2040076 | 3/2009 | |
| EP | 2376689 A1 | 10/2011 | |
| GB | 1356346 | 6/1974 | |
| GB | 2381482 | 5/2003 | |
| JP | 01-291164 A | 11/1989 | |
| JP | 03-503212 A | 7/1991 | |
| JP | 5416222 B2 | 2/2014 | |
| WO | WO 2003/020924 | 5/2007 | |
| WO | WO 2009/090174 | 7/2009 | |
| WO | 2009/155612 A2 | 12/2009 | |
| WO | 2010-074773 A1 | 7/2010 | |

OTHER PUBLICATIONS

GE Healthcare, Ficoll PM70 and Ficoll PM400, 2007, pp. 1-6, retrieved from https://www.gelifesciences.com/gehcls_images/GELS/Related%20Content/Files/1314735988470/litdoc18115827AB_20110830230116.pdf on Mar. 27, 2015.*
Santa Cruz Biotechnology, MSDS Polybrene®, 2 pgs, 2009, retrieved from http://datasheets.scbt.com/sc-134220.pdf on Mar. 29, 2015.*
Supplementary European Search Report for EP Application No. 12 84 6138 dated May 8, 2015 (3 pages).

* cited by examiner

*Primary Examiner* — Andrea S Grossman
(74) *Attorney, Agent, or Firm* — Eversheds Sutherland (US) LLP

(57) ABSTRACT

The invention discloses a cellulose or glass fiber paper for preservation of biological samples, which comprises 4-30 wt % of a hydrophilic branched carbohydrate polymer. It also discloses a method for preservation of biological samples by applying and drying them on the paper.

19 Claims, No Drawings

SAMPLE PRESERVATION METHOD AND SAMPLE PRESERVATION SUBSTRATE

CROSS-REFERENCE TO RELATED APPLICATIONS

This application is a filing under 35 U.S.C. 371 of international application number PCT/SE2012/051168, filed Oct. 29, 2012, published on May 10, 2013 as WO 2013/066249, which claims priority to application number 1118731.7 filed in Great Britain on Oct. 31, 2011.

TECHNICAL FIELD OF THE INVENTION

The present invention relates to methods for sample preservation, and more particularly to sample preservation on paper substrates. The invention also relates to paper substrates for sample preservation and to methods of manufacturing such substrates.

BACKGROUND OF THE INVENTION

Increasing use is being made of paper substrates in the analysis and/or storage of biological materials. One such area of use concerns the growing need for rapid analysis of large quantities of blood samples in pharmacokinetic research, for example in drug discovery programmes. It is obviously desirable for such uses that the paper combines satisfactory mechanical properties with an ability to hold the biological material of interest in such a way that it can be subjected to analysis and/or further processing following storage. Examples of such papers are those known as FTA and FTA Elute (Whatman, part of GE Healthcare) described for example in U.S. Pat. Nos. 5,756,126 and 5,939,259. These papers have been impregnated with chemicals to provide cell lysis, preservation of nucleic acids and to facilitate further processing of nucleic acids.

However, these papers are specifically designed for nucleic acid analysis. There is also a strong interest in the use of paper substrates for processing of samples where proteins are analysed. Proteins differ from nucleic acids i.a. in that they are prone to denaturation and consequent loss of biological activity upon drying and storage. Proteins to be analysed, e.g. biomarkers or drugs in blood, are also often present in very low amounts and prone to masking by additives. In particular, analytical techniques such as mass spectroscopy and immunoassays can be affected by chemical additives. Plain untreated cellulose papers such as the 903 or 31ETF papers (Whatman, part of GE Healthcare) are used for preservation of blood samples followed by protein analysis, but do not always give the desirable analytical recoveries and biological activities of e.g. sensitive proteins. Addition of different fillers such as polyvinyl alcohol, Ficoll and sugars has been mentioned as a way to stabilize proteins in e.g. US2010/0209957 and WO2003/020924. These compositions are however also limited in the recoveries and activities of sensitive proteins.

In addition to stabilization for analytical purposes, there is also a need for stabilization of proteins and other sensitive biomolecules in therapeutic and diagnostic contexts, e.g. in storage of pharmaceutical formulations or diagnostic reagents in dry form.

Accordingly there is a need for sample preservation methods and sample preservation substrates with improved performance.

SUMMARY OF THE INVENTION

One aspect of the invention is to provide sample application substrate capable of receiving a sample, such as a liquid biological sample, and providing a high recovery of biologically active proteins after drying and storage. This is achieved with a paper as described herein.

One advantage is that a high recovery of sensitive proteins can be obtained. Further advantages are that homogenous circular sample spots can be obtained and that liquid samples are well absorbed by the substrate.

Another aspect of the invention is to provide a sample collection device capable of receiving a sample and providing a high recovery of biologically active proteins after drying and storage. This is achieved with a sample collection device as described herein.

A third aspect of the invention is to provide a method of applying a sample to a sample application substrate which provides a high recovery of biologically active proteins after drying and storage. This is achieved by a method as described herein.

A fourth aspect of the invention is to provide a method of preparing a paper substrate capable of receiving a sample and after drying and storage providing a high recovery of biologically active proteins. This is achieved with a method as described herein.

Further suitable embodiments of the invention are described in the dependent claims.

DEFINITIONS

The term "paper" as used herein means a fibrous web or sheet material. Paper comprises fibres, e.g. cellulose or glass fibres, and optionally other components, such as e.g. particulate fillers, wet strength or dry strength additives, retention agents etc.

The term "carbohydrate polymer" as used herein means a polymer with a main chain comprising carbohydrate moieties, also called saccharide moieties. A carbohydrate polymer can be a polysaccharide (i.e. a polymer with a main chain consisting of linked carbohydrate/saccharide moieties), a modified polysaccharide (i.e. a polysaccharide with substituents or grafted side chains) or a synthetic carbohydrate polymer, where carbohydrate moieties are linked to each other via synthetic linking units. A hydrophilic carbohydrate polymer is in this context either water soluble or water swellable, wherein in the latter case the polymer may be prevented from dissolving in water by crosslinks or by tethers to one or more surfaces.

The term "analyte" as used herein means a substance undergoing or intended to undergo detection, quantification, analysis, characterisation and/or evaluation.

The term "contaminant" as used herein means a substance having the potential to interfere with the detection, quantification, analysis, characterisation or evaluation of one or more analytes. An analyte can also be a contaminant if it has the potential to interfere with the detection, quantification, analysis, characterisation or evaluation of another analyte.

The term "sample" as used herein means a portion of a fluid, liquid, semisolid or solid material.

The term "ligand" as used herein means a chemical species capable of binding or attracting another species. If a ligand is attached to a solid surface, dissolved substances may bind to or be retained by the surface, depending on the selectivity of the ligand for each substance.

DETAILED DESCRIPTION OF EMBODIMENTS

In one aspect the present invention discloses a paper useful as a sample application substrate for preservation of biological samples. The paper has a surface weight of 40-800 g/m², it comprises cellulose fibres and/or glass fibres, and it also comprises 4-30 wt % of a hydrophilic or water soluble branched carbohydrate polymer. The surface weight is determined by weighing an air-dry sheet of predetermined area of the paper (e.g. 10.0×10.0 cm) and dividing the weight (g) with the sheet area (m²). The branched carbohydrate polymer can e.g. have a degree of branching of 0.05-1, such as 0.10-1, 0.20-1 or 0.30-1. The degree of branching (DB) is defined as $DB=nD/(nD+L)$, where D is the number of branch-point monomer units in a polymer molecule, n is the average number of branches extending from each branch-point and L is the number of linear (non-branching) monomer units in the polymer molecule. The degree of branching can be determined according to methods known in the art, e.g. by NMR spectroscopy, degradation analysis, and by gel filtration using a light scattering or viscosity detector. (K Granath: J Coll Sci 13, 308 1958; J Smit et al: Macromolecules 25, 3585 1992). Examples of branched carbohydrate polymers include dextrans, Ficoll and branched hemicelluloses such as xylans. An advantage of having a carbohydrate polymer in the paper is that it provides a protective effect on proteins, possibly by preventing denaturation. Branched carbohydrate polymers have particularly good protective effect and they are also easier to apply due to their lower viscosities. An advantage of having at least 4% of the polymer in the paper is that good protection is obtained over this level. An advantage of having no more than 30% polymer in the paper is that the spots formed by application of liquid biological samples, e.g. blood, on the paper are circular and homogeneous below this level. If the polymer content is too high, the spot shape will be irregular, causing difficulties in the subsequent sampling from the paper. The absorption of the samples into the paper is also better if the polymer content does not exceed 30%. At too high polymer contents, a blood spot will not be completely absorbed by the paper, so that a film of dried blood is formed on the paper surface. This means that part of the dried blood is not in contact with the preserving polymer and there is also a risk of losing chips of dried blood so that a quantitative sampling is not possible. The combination of protective effect and spot shape/homogeneity/absorption is particularly good if the amount of the branched carbohydrate polymer in the paper is 10-25 wt %, such as 12-25 wt %. Branched carbohydrate polymers are also advantageous from the solubility point of view in that they are more readily dissolved in water than linear carbohydrate polymers such as amylose or cellulose. They are also easier to dissolve than synthetic non-carbohydrate hydroxypolymers such as polyvinyl alcohol. Ease of dissolution is a distinct advantage during extraction of the proteins from the paper.

In some embodiments, the hydrophilic or water soluble branched carbohydrate polymer has an average molecular weight of 15-800 kDa, such as 20-500 kDa. It can in particular have an average molecular weight of 70-400 kDa, such as about 70 kDa or about 400 kDa. The protective effect is better if the molecular weight is not too low and with very high molecular weights, viscosity can become an issue both during impregnation of the paper and during extraction of the proteins from the paper.

In some embodiments, the branched carbohydrate polymer comprises a dextran. Dextrans are branched α (1→6)-linked glucans and the most common variety, produced from sucrose solutions by the Leuconostoc mesenteroides NRRL B-512(F) bacteria, have side chains attached to the 3 positions of the backbone glucose units with approx. 5% of the glucose units forming branching points. This gives a degree of branching of 0.05 as defined above. 10 wt % aqueous dextran solutions have a Newtonian rheology, with viscosities about 2 mPas (Mw 10 kDa), 4 mPas (40 kDa) and 10 mPas (70 kDa). B-512(F) dextrans are commercially available from e.g. Pharmacosmos A/S (Denmark) or TdB Consultancy AB (Sweden). It is also possible to use dextran derivatives such as e.g dextran sulfate, carboxymethyl (CM) dextran or diethylaminoethyl (DEAE) dextran. Such derivatives are available from e.g. TdB Consultancy AB. In alternative embodiments the branched carbohydrate polymer does not comprise dextran.

In certain embodiments, the branched carbohydrate polymer comprises a copolymer of a mono- or disaccharide with a bifunctional epoxide reagent. Such polymers will be highly branched due to the multitude of reactive hydroxyl groups on each mono/disaccharide. Depending on the reaction conditions used, the degree of branching can be from about 0.2 up to almost 1. A particular example of these polymers is sucrose-epichlorohydrin polymers, prepared e.g. according to the methods of U.S. Pat. No. 3,300,474. A commercially available sucrose-epichlorohydrin polymer is Ficoll™, which is also called polysucrose (CAS No. 25702-74-3). It is available from GE Healthcare (Sweden) in average molecular weights of 70 and 400 kDa. 10 wt % aqueous solutions of Ficoll have a Newtonian rheology, with a viscosity of about 3 mPas (70 kDa) and about 5 mPas (400 kDa). The low viscosities are presumably due to the highly branched structure of the polymer molecules. Charged varieties of Ficoll such as CM Ficoll and DEAE Ficoll can be obtained e.g. from TdB Consultancy AB (Sweden)

In some embodiments, a 10 wt % water solution of the branched carbohydrate polymer has a viscosity of 1-10 mPas, such as 1-5 mPas, at 20° C. A low viscosity is advantageous from several points of view. It facilitates impregnation of the base paper and ensures that the distribution of the polymer in the paper is homogeneous. It also facilitates the extraction and further handling of the extracted solutions. Low viscosities may also be beneficial in that the sample is absorbed more easily by the paper and in that the paper does not get sticky.

In certain embodiments, the content of water extractables in said paper is 0-25 wt %, such as 0.1-5 wt % or 3-20 wt %. The amount of water extractables is determined by immersing a piece of the paper in water (water-paper volume ratio at least 20:1) and agitating gently at room temperature for 2 h. The paper is then collected on e.g. a glass filter, dried and weighed. The water extractables are calculated as the % weight loss. Water extractable amounts less than about 1% may be determined by e.g total organic carbon analysis of the water extract after filtration through a glass fiber filter free from extractables. Having a low amount of water extractables can be an advantage when analytical techniques sensitive to the presence of carbohydrate polymers or other extractables are used for analysis of the protein(s). In therapeutic applications it is also desirable to have low amounts of extractables. Very low amounts of extractables can be achieved when the carbohydrate polymer is covalently coupled to the paper fibres and/or crosslinked to itself.

In some embodiments, the paper comprises 5-300 micromole/g, such as 5-50, 5-100 or 50-300 micromole/g negatively or positively charged groups. Negatively charged groups can be e.g. carboxylate groups, sulfonate groups or sulfate groups, while positively charged groups can be e.g. amine or quaternary ammonium groups. The presence of these groups appears to improve the protective effect of the branched carbohydrate polymer. The negatively or positively charged groups can be covalently bound to the carbohydrate polymer or they can be covalently bound to the cellulose or glass fibres of the base paper. If the negatively charged groups are bound to the fibres or to a carbohydrate polymer which is crosslinked or covalently coupled to the fibres, the charged groups are not water extractable. This can be an advantage, particularly if mass spectroscopy is used as a method of analysis and also in a therapeutic context. Amounts of negatively or positively charged groups can be determined e.g. by well-known titration methods. Additionally, sulfonate, sulfate, amine and quaternary ammonium groups can be determined by elementary analysis, provided that non-charged sulfur or nitrogen containing species are not present.

In certain embodiments the paper comprises at least one dried biological sample, such as a dried blood sample. Blood and other biological materials, e.g. serum, plasma, urine, cerebrospinal fluid, bone marrow, biopsies etc. can be applied to the paper and dried for storage and subsequent analysis or other use. The dried biological sample can also be a pharmaceutical formulation or a diagnostic reagent, comprising at least one protein or other sensitive biomolecule.

In one aspect the present invention discloses a sample collection device, comprising the paper as described above. The sample collection can be a paper card, with one or more sample application areas printed or otherwise indicated on the card. There may be indicator dyes in these areas to show if a non-coloured sample has been applied or not. The device may also include a card holder, to e.g. facilitate automatized handling in racks etc. and it may include various forms of sampling features to facilitate the collection of the sample.

In one aspect the present invention discloses a method for preservation of at least one biological sample, comprising the steps of:
a) providing a biological sample,
b) applying said biological sample on the paper described above, and
c) drying said paper with said biological sample, The biological sample may be a biological fluid, e.g. blood, serum, plasma, urine, cerebrospinal fluid, bone marrow etc. but it may also be a solid or semi-solid such as tissue biopsies etc. It can also be a pharmaceutical formulation or a diagnostic reagent, comprising at least one protein or other sensitive biomolecule.

An advantage of applying a fluid sample is that it is absorbed by the paper structure and comes into direct contact with the protective branched carbohydrate polymer. The drying can be passive, when the paper with the sample/formulation/reagent is simply left to dry, or it can be active, when it is subjected e.g. to moderately elevated temperatures, infrared radiation and/or a stream of air or other gas. The drying can advantageously be performed at temperatures of 15-35° C., such as 15-25° C. After drying, the residual moisture content of the paper, or a sample application area with a sample, can be less than about 20 wt. %, such as less than about 10 wt. %.

In certain embodiments the method comprises a step d) of storing the dried paper with the biological sample for at least one week, such as at least one month or at least one year. The storage temperature in step d) can be at least 0° C., such as 0-40° C. or 20-40° C. It is an advantage of the method of the invention that the structure and biological activity of sensitive proteins can be maintained over long times without the need of freezing or even without refrigeration. The paper with the sample(s) can advantageously be stored at a relative humidity between 0 and 70%, such as between 0 and 50% or between 0 and 20%. The relative humidity can e.g. be controlled by storing the paper with the samples together with a desiccant in a closed container, such as a closed plastic bag.

In some embodiments the method comprises a step e) of extracting at least one protein from said paper after storage and analyzing said protein. The extraction can be made e.g. by punching out small parts of the paper with dried sample and immersing these in an aqueous liquid, e.g. a buffer for a period of e.g. 1 h-48 h. The immersion may be performed under agitation and the temperature may e.g. be 0° C. to 30° C. If the immersion time is more than 1-2 h, it is an advantage if the immersion temperature is 0-8° C. to minimize any degradation of sensitive proteins in solution.

In some embodiments the method comprises a step e') of extracting said paper after storage and using the extract as a medicament. In this case, the biological sample stored on the paper is suitably a pharmaceutical formulation and the application of the formulation to the paper, the drying, the storage and the extraction can be performed under aseptic conditions.

In certain embodiments the protein is a storage-sensitive protein, which can be defined as a protein giving less than about 60%, or less than about 40%, recovery of the protein in a biologically active state after storage in plain paper with a desiccant for 1 week at 37° C. This value can preferably be determined with the protein being present in a dried blood spot (DBS) on the paper. One example of a storage-sensitive protein is C-reactive protein (CRP), but also proteins such as apolipoprotein A-1, IgE have been reported as being sensitive to storage in DBS (T McDade et al: Demography 44, 899 2007).

In some embodiments in step e) of the method, the recovery of said protein in a biologically active state is at least 60%, at least 70%, at least 80%, at least 90% or at least 95%.

In some embodiments the protein is analyzed in step e) by an immunoassay, by mass spectrometry or an enzyme activity assay. Immunoassays, e.g. ELISA, are commonly used to determine the concentration of particular proteins. As they rely on the antibody-binding properties of the protein it is essential that the protein is biologically active (i.e. not denatured), in particular when assays with antibodies against conformation epitopes are used. Enzymes are generally sensitive to denaturation and a denatured enzyme will show no activity or a strongly reduced activity in an assay. Mass spectrometry (MS) is another common analysis technique for proteins, which requires that the sample applied to the mass spectrometer does not contain leachables from the paper, e.g. detergents. The branched polysaccharide polymers used can easily be removed from the sample by conventional work-up methods for MS analysis, e.g. reversed phase chromatography, and hence they do not produce interference.

In one aspect the present invention discloses a method of manufacturing a paper for preservation of biological samples. The method comprises the following steps:
a) provide cellulose fibres or glass fibres either in an aqueous suspension or in the form of a base paper,
b) contact the fibres, either in suspension or as a base paper, with a solution comprising 2-60 wt % of a water soluble branched carbohydrate polymer,
c) if the fibres are in aqueous suspension, form a paper sheet from the fibres, and
d) dry the paper.

The contacting of a fibre suspension with the polymer solution can take place simply by mixing the suspension and the solution or by dissolving the polymer in the suspension.

The contacting of a base paper with the polymer solution can take place as an impregnation step as described below. If the polymer is to be covalently coupled, the solution can have a concentration of e.g. 20-60 wt % polymer, while in the case of impregnation of a base paper with a branched carbohydrate polymer under conditions not giving covalent coupling, the concentration can be e.g. 2-15 wt % or 4-10 wt %. Formation of a paper sheet can be done according to methods well known in the art, either by handsheet formation or by formation on a paper machine, e.g. a mould or Fourdrinier machine. The drying can be passive, when the paper with the sample is simply left to dry, or it can be active, when it is subjected e.g. to elevated temperatures, infrared radiation and/or a stream of air or other gas. The drying can advantageously be performed at temperatures of 20-100° C., such as 20-60° C. After drying, the residual moisture content of the paper, can be less than about 20 wt. %, such as less than about 10 wt. %. In a production setting, the drying can suitably be made in an on-line dryer applied e.g. after an immersion coater or the formation unit of a paper machine.

In one aspect the present invention discloses a method of manufacturing a paper for preservation of biological samples. The method comprises the following steps:
a) provide a base paper having a surface weight of 40-800 g/m$^2$, which comprises cellulose fibres or glass fibres,
b) impregnate the base paper with a solution which comprises 2-60 wt % of a water soluble branched carbohydrate polymer with an average molecular weight of 15-800 kDa
c) dry the impregnated paper.

The impregnation can be made by immersing a sheet of base paper in the solution or it can be made in a roll-to-roll process using various types of impregnation equipment known in the art, such as e.g. immersion coaters. If the polymer is to be covalently coupled, the solution can have a concentration of e.g. 20-60 wt % polymer, while in the case of impregnation with a branched carbohydrate polymer under conditions not giving covalent coupling, the concentration can suitably be e.g. 2-15 wt % or 4-10 wt %. The drying can be passive, when the paper with the sample is simply left to dry, or it can be active, when it is subjected e.g. to elevated temperatures, infrared radiation and/or a stream of air or other gas. The drying can advantageously be performed at temperatures of 20-100° C., such as 20-60° C. After drying, the residual moisture content of the paper, can be less than about 20 wt. %, such as less than about 10 wt. %. In a production setting, the drying can suitably be made in an on-line dryer applied e.g. after an immersion coater.

In certain embodiments the branched carbohydrate polymer comprises dextran or a copolymer of a mono- or disaccharide with a bifunctional epoxide reagent as described above. The branched carbohydrate polymer can specifically be a sucrose-epichlorohydrin polymer, such as Ficoll. The branched carbohydrate polymer can have an average molecular weight of 20-500 kDa or 70-400 kDa, such as 20 kDa, 70 kDa or 400 kDa.

In some embodiments the solution of the branched carbohydrate polymer has a viscosity of 1-20 mPas, such as 1-10 mPas at 20° C. As stated above, low viscosity solutions facilitate impregnation and also bring about further functional advantages.

In certain embodiments the base paper comprises 5-300 micromole/g negatively charged groups, such as carboxylate groups. The negatively charged groups may be introduced in the paper e.g. by oxidation processes or by covalent coupling of charged species, such as chloroacetic acid, bromoacetic acid, sodium vinylsulphonate etc. according to known techniques for preparing polysaccharide-based cation exchangers.

In certain embodiments the fibres or the base paper are chemically activated and the method comprises a step of reacting the fibres or the base paper with the branched carbohydrate polymer. An advantage of using activated fibres/base paper is that a covalent coupling of the carbohydrate polymer can be achieved. This has the advantage that interference of extracted polymer with analysis methods can be avoided. Having a covalently coupled polymer can also be beneficial for the preservation of proteins. The activation can be accomplished by several different methods, e.g. by reaction with an epihalohydrin (e.g. epichlorohydrin) or a diepoxide, in which case the activated fibres or the activated paper will comprise reactive epoxy groups. Alternatively, the fibres/the paper can be activated by tosylation, tresylation or mesylation, creating the corresponding reactive leaving groups, or they can be activated with divinylsulphone or by allylation followed by either bromination of the allyl groups or direct coupling on the allyls, etc. It is advantageous if the activated groups are reactive towards hydroxyl groups in the branched carbohydrate polymer, but they can also be reactive to specific functional groups introduced in the polymer, e.g. amines or aminooxy groups (reactive e.g. towards aldehydes) or carboxyl groups (reactive towards carbodiimides) etc. Glass fibres can be activated by reaction with silanes, e.g. epoxy silanes. The reaction between the carbohydrate polymer and the activated fibres/paper can take place directly in the suspension, optionally after heating and/or adjusting pH to accelerate the reaction. It can also take place during or after drying of the paper, e.g at elevated temperature.

In certain embodiments the method also comprises a step of washing the fibres or the base paper after the reaction step. This removes unreacted polymer from the system and is a further way to ensure that the polymer does not leach out and interfere with any analysis methods. The washing can suitably take place after the reaction described above.

EXAMPLES

Materials

31 ETF base paper (Whatman, part of GE Healthcare)
903 base paper (Whatman, part of GE Healthcare)
Dextran T3.5 (3.5 kDa), Dextran 20 (20 kDa), Dextran 70 (70 kDa), Dextran 110 (110 kDa) (GE Healthcare)
Ficoll PM20 (20 kDa), Ficoll PM70 (70 kDa), Ficoll PM400 (400 kDa) (GE Healthcare)
DEAE Ficoll PM70 (70 kDa), CM Ficoll PM70 (70 kDa) (TdB Consultancy AB)

Example 1—Soaking in Ficoll and Dextran Solutions

Strips were cut from the chosen paper, the air-dry weight recorded and the paper placed in 90 mm plastic Petri dishes, two strips in each. The desired aqueous solution (25 mL) of Ficoll or dextran was added and the dish placed on a shaker and agitated at 100 rpm for 1 h 45 min. The prototypes were then removed from the Petri dishes and placed horizontally in a Whatman 903 Dry Rak and allowed to dry at room temperature overnight. The weight was recorded and the increase in mass calculated. Finally the prototypes were tagged with a plastic label and stored in 90 mm Petri dishes for further DBS analysis.

TABLE 1

Weight increase for the prepared prototypes, samples in duplicates

| Compound | Concentration in solution (wt %) | Weight increase of paper (wt %) |
|---|---|---|
| Ficoll PM400 | 10 | 25 |
| Ficoll PM400 | 7 | 15 |
| Ficoll PM400 | 5 | 12 |
| Ficoll PM400 | 2 | 4 |
| Ficoll PM70 | 10 | 26 |
| Ficoll PM70 | 7 | 16 |
| Ficoll PM70 | 5 | 11 |
| Ficoll PM70 | 2 | 3 |
| Ficoll PM70 | 1 | 1 |
| Dextran 110 | 10 | 27 |
| Dextran 110 | 7 | 17 |
| Dextran 110 | 5 | 12 |
| Dextran 110 | 2 | 4 |
| Dextran 110 | 1 | 1 |
| Dextran 20 | 10 | 26 |
| Dextran 20 | 7 | 18 |
| Dextran 20 | 5 | 12 |
| Dextran 20 | 2 | 4 |
| Dextran 20 | 1 | 2 |
| Dextran T3.5 | 10 | 26 |
| Dextran T3.5 | 7 | 18 |
| Dextran T3.5 | 5 | 12 |
| Dextran T3.5 | 2 | 4 |
| Dextran T3.5 | 1 | 2 |

The mass increase for all prototypes is very similar, for example when a 10 wt % solution has been used the weight increase is 25-27% regardless which polymer has been used.

Example 2—Covalent Coupling of Ficoll and Dextran

Epichlorohydrin (ECH) Coupling of Ficoll PM70

In a typical experiment a paper strip was cut from 31 Etf paper, which had been placed at 60° C. and dried at least overnight prior to the experiment. Plastic nets were cut to cover the inside of 150 mL glass reactor and the paper strip was sandwiched between them. To the reactor water (103.2 mL), 50% NaOH (10.6 mL) and ECH (16.1 mL) were added and the solution stirred for 120 min at 30° C. The reaction mixture was decanted and 130 mL of water added and stirring continued for 20 min. This was repeated twice.

Ficoll PM70 solution (100 mL) with desired concentration was added to the reactor and the solution stirred for 15 minutes prior to the addition of 50% NaOH (2.916 mL). The reaction was stirred at 30° C. overnight. After 20 h the reaction mixture was decanted and 130 mL of water added and stirring continued for 20 min. The paper prototype was removed from the reactor and placed in a glass beaker (600 mL) and water (300 mL) was added covering the prototype completely. The beaker was slowly agitated on a shaker at ~80 rpm for 20 min after which the water was decanted and fresh water added. This was repeated three times. The paper was left to dry in the fume hood overnight on plastic nets to ensure the prototype was flat. The prototypes were stored in Zip-Lock bags until analysed further.

ECH Coupling of Ficoll PM70 on Repulped Fibre

In a typical experiment about 15 g of 31 ETF paper was torn to small pieces and thrown into a blender together with water (~500 ml) and mixed harshly for about 3 min into a pulp. The pulp slush was poured into a sintered glass funnel (P2) and most of the water removed. The weight was recorded (~80 g) and the slightly moist pulp was transferred to a 500 mL round bottom flask (RBF). To the RBF water (142 mL) and 50% NaOH (25 mL) were added and the mixture stirred for 15 min using an overhead stirrer. Whilst stirring ECH (30 mL) was added and the water bath set to 30° C. The mixture was then stirred for additionally 2 h.

The reaction was terminated by transferring the pulp to a sintered glass funnel and washing it with 5× Water. The pulp was stirred after each wash and the suction started when the water started to drop through the funnel. The drained pulp was then transferred to a new 500 mL RBF which was charged with Ficoll PM70 solution (25 mL). The mixture was stirred for ~20 min before addition of 50% NaOH (8.75 mL). Stirring was continued overnight at 30° C.

After about 20 h the reactions were terminated and the fibre prototype washed on a glass filter using 5× Water. This turned out to be a quite tedious procedure especially for the high concentration fibres. In the last washing step the still fairly wet fibre was transferred to a Zip-Lock bag and used for handsheet paper production. Unmodified 31Etf fibre was also prepared and used for handsheet production.

Soaking and ECH Coupling of Ficoll PM20 and Soaking of Dextran 70

Experiments were performed as described above with some alterations for the coupled Ficoll PM20 prototypes. Smaller glass reactors (100 mL) were used and the reaction volumes decreased; for the activation water (23.83 mL), 50% NaOH (2.45 mL) and ECH (3.72 mL) was used. The coupling was performed using Ficoll PM20 solution (30 mL) and 50% NaOH (744.8 µL).

The coupled DEAE-Ficoll PM70 prototypes were sent for elemental analysis (% N), Table 2. According to the analysis certificate provided by TdB Consultancy the Nitrogen content of DEAE-Ficoll PM70 is 3.6%, so a 0.086% N content in the paper should correspond to a DEAE-Ficoll PM70 content of 2.4 wt %.

TABLE 2

Elemental analysis of the DEAE-Ficoll prototypes (% N)

| Prototype | Paper | Ligand | Coupling Solution(wt %) | N % (g/g) |
|---|---|---|---|---|
| U2612068E | 31Etf | DEAE-Ficoll PM70 | 20 | <0.01 |
| U2612068F | 31Etf | DEAE-Ficoll PM70 | 50 | 0.086 |

Example 3—Recovery of C-Reactive Protein from Dried Blood Spots

Blood samples (4 µl/spot) were spotted on various types of soaked and covalently coupled prototypes and reference papers. After drying spots were punched out and extracted according to conditions used in previous studies (section 2). The amount of CRP and total protein was determined by ELISA and A280 respectively. The recovery is calculated from the amount in reference blood samples (n=3).

Spotting and Storage of DBS Samples

4 µl blood aliquots were spotted on the different prototypes in triplicates DBS dried in RT for 4 h and stored (−20 C.) with drying agent in sealed bags until use. 4 µl blood aliquots were stored in 0.5 ml tubes for reference purpose (stored −20° C.).

DBS Extraction

Blood spots were punched in triplicate with punch pliers. The size was chosen to punch complete spot (5 mm diameter). The discs were put in 96-well plates and extracted with 100 µl PBS-T during shaking (~400 rpm), 1 h RT, over night+4 C., 1 h RT. The plate was sealed during incubation and centrifuged at 3700 rpm in plate centrifuge prior to sample analysis.

CRP ELISA/A280 Measurement

The Human CRP ELISA Kit was used according to manufactures instruction.

Reference blood aliquots (n=3) were diluted with 100 μl PBS-T. References and extracted samples were then further diluted 1:10 in CRP wash buffer to a final volume of 200 μl in an UV-plate. The absorbance at 280 nm was measured prior to CRP analysis for calculation of protein recovery. DBS samples were analysed as single samples and blood references in duplicates in the CRP ELISA assay.

In the A280 measurement DBS samples and blood references in screening study part II were analysed as single samples. Blood references were analysed in duplicates in part I of the study.

CRP Recovery $$\text{Recovery \%} = \left(\frac{\text{Conc CRP in sample}}{\text{Conc CRP in blood reference (average)}}\right) \times 100$$

Protein Recovery

The absorbance at 280 nm was used as a measure of overall protein recovery of the extracted samples.

$$\text{Recovery \%} = \left(\frac{\text{Sample } A280}{\text{Blood reference } A280 \text{ (average)}}\right) \times 100$$

The first part of the prototype screening (table 3) contained prototypes soaked with Ficoll PM400, PM70 and PM20. All soaked prototypes gave approximately 20% higher recovery compared to the reference paper.

TABLE 3

Average CRP recovery (triplicates) in DBS extract from Ficoll modified papers.

| Paper | Concentration in soaking solution (wt %) | CRP recovery (%) |
|---|---|---|
| Plain 31ETF paper (reference) | — | 81.2 |
| 31ETF + Ficoll PM400 | 7 | 102.6 |
| 31ETF + Ficoll PM70 | 7 | 98.5 |
| 31ETF + Ficoll PM70 | 5 | 100.5 |
| 31ETF + Ficoll PM20 | 10 | 104.0 |
| 31ETF + Ficoll PM20 | 7 | 105.1 |
| 31ETF + Ficoll PM20 | 5 | 100.2 |

TABLE 4

Average CRP recovery (triplicates) in DBS extract from DBS paper prototypes.

| Paper | Concentration in soaking/coupling solution (wt %) | CRP recovery (%) |
|---|---|---|
| Plain 31ETF paper (reference) | — | 73.4 |
| Plain 903 paper (reference) | — | 70.6 |
| Handsheet from repulped 31ETF, treated with ECH | — | 61.1 |
| 31ETF soaked w Ficoll PM70 | 7 | 86.8 |
| 903 soaked w Ficoll PM70 | 5 | 84.2 |
| 903 soaked w Ficoll PM70 | 7 | 100.1 |
| Handsheet from repulped 31ETF, with ECH-coupled Ficoll PM70 | 30 | 81.9 |
| Handsheet from repulped 31ETF, with ECH-coupled Ficoll PM70 | 50 | 84.8 |
| 31ETF soaked w CM Ficoll PM70 | 5 | 92.1 |
| 31ETF soaked w CM Ficoll PM70 | 7 | 93.0 |
| 31ETF with ECH-coupled CM Ficoll PM70 | 50 | 70.3 |
| 31ETF soaked w DEAE Ficoll PM70 | 5 | 107.2 |
| 31ETF soaked w DEAE Ficoll PM70 | 7 | 102.4 |
| 31ETF with ECH-coupled DEAE Ficoll PM70 | 50 | 75.6 |
| 31ETF soaked w Dextran 70 | 5 | 91.0 |
| 31ETF soaked w Dextran 70 | 7 | 90.1 |
| 31ETF with ECH-coupled Dextran 70 | 30 | 62.2 |
| 31ETF with ECH-coupled Dextran 70 | 50 | 62.6 |
| 31ETF soaked w Dextran 70/Ficoll PM70 1:4 | 7 | 94.6 |
| 31ETF soaked w Dextran 70/Ficoll PM70 4:1 | 7 | 95.5 |

The second part of the prototype screening (table 4) contained a wide variety of mainly Ficoll prototypes. Soaked prototypes gave also in this study clearly higher recovery compared with coupled prototypes in general. Also when coupling was done on the paper fibres an increased CRP recovery was obtained.

Mixtures of Ficoll and dextran also seem to have a stabilizing effect on the CRP molecule. The ratio between Ficoll and dextran was not critical.

Even Ficoll prototypes with charged groups were working well in this study.

Prototypes soaked with charged Ficoll derivatives worked well in the ELISA application. For MS applications, the charged polymer may need to be removed from the sample first.

The recovery of total amount of protein (not shown) was good from all prototypes and the variation seen reflects most likely the variation in spotted volume.

Example 4—Stability of C-Reactive Protein, Leptin and β2 Glycoprotein-1 in Dried Blood Spots A forced stability study has been conducted of modified cellulose papers aimed for Dry Blood Spot (DBS) samples. DBS samples were spotted on soaked and covalently coupled Ficoll prototypes to monitor stabilizing effect on C-reactive protein (CRP), Leptin and β2 Glycoprotein-1 after storage one week at −20° C. and 37° C. respectively. Commercial available ELISA kits have been used for evaluation. The goal was to find modification that is beneficial for more proteins than CRP, for which high recovery (compared to reference paper) has been established previously.

The result showed 10-20% higher recovery of CRP from soaked paper prototypes compared to prototypes modified by covalent coupling but no effect on leptin recovery. Soaked Ficoll PM400 was almost as good as untreated paper for β2GP1 and beneficial for both CRP and β2GP1 during storage at elevated temperature with less decrease in recovery compared to other prototypes.

To summarize the result it can be concluded that paper soaked with Ficoll PM400 seems beneficial for certain proteins upon storage as DBS.

Spotting and Storage of DBS Samples

15 µl blood aliquots were spotted on the different prototypes in triplicates. DBS were dried in RT for 4 h and the papers were then stored at 37° C. in sealed bags with desiccant packets for one week. 15 µl blood aliquots were stored in 0.5 ml tubes for reference purpose (−20° C.).

DBS Extraction

Spots were punched out (9 mm Ø) and extracted in 24 well plates with 400 µl buffer during 1 h in RT (mixing ~500 rpm), +4° C. overnight and 1 h RT (mixing ~500 rpm). The plate was sealed during incubation and centrifuged at 3700 rpm in plate centrifuge prior to sample analyse. Sample for CRP and A280 analysis was removed and the sample plates were stored −20° C. The extracted discs were removed before sample outtake for leptin and β2GP1 analysis.

CRP ELISA/A280 Measurement

The Human CRP ELISA Kit was used according to manufactures instruction except dilution recommendations (serum to be diluted 1:4000). Sample was diluted 1:270 as in previous studies. Reference blood aliquots (n=3) were diluted with 385 µl PBS-T. References and extracted samples were then further diluted 1:10 in CRP wash buffer to a final volume of 200 µl in an UV-plate.

a pre-study (1:50, 1:500 and 1:2500). Dilution 1:500 ended in the lower third of the standard curve and hence 1:250 was assumed to work well for the final study and hence used. DBS samples were analysed as single samples and blood references in duplicates.

CRP/Leptin/β2GP1 Recovery $$\text{Recovery \%} = \left( \frac{\text{Conc CR/leptin/}\beta 2GP1 \text{ in sample}}{\text{Conc CRP/leptin/}\beta 2GP1 \text{ in blood reference (average)}} \right) \times 100$$

Protein Recovery

The absorbance at 280 nm was used as a measure of overall protein recovery of the extracted samples.

$$\text{Recovery \%} = \left( \frac{\text{Sample } A280}{\text{Blood reference } A280 \text{ (average)}} \right) \times 100$$

The stability of three different proteins in DBS from paper prototypes have been monitored by ELISA. Table 2 shows a compressed summary of the result from the study.

TABLE 5

Average recovery (n = 3) of three proteins obtained by extraction from DBS collected on DBS paper prototypes stored for one week at 37 C and analysed by ELISA. Recovery is calculated as % of amount obtained in blood reference sample (n = 3, analysed in duplicate).

| DBS paper prototype | CRP recovery % | StDev | Leptin recovery % | StDev | β2 GP1 recovery % | StDev | Protein recovery % | StDev |
|---|---|---|---|---|---|---|---|---|
| 31 ETF | 52.0 | 0.9 | 65.9 | 6.5 | 75.9 | 0.8 | 74.6 | 2.4 |
| 31 ETF fibre | 51.1 | 1.7 | 57.9 | 1.5 | 76.8 | 1.3 | 77.2 | 2.5 |
| PM20 5% | 55.1 | 6.7 | 60.5 | 9.9 | 85.7 | 12.4 | 77.2 | 6.0 |
| PM20 ECH 50% | 55.7 | 5.3 | 53.8 | 5.7 | 88.6 | 11.6 | 87.1 | 14.9 |
| PM70 5% | 67.1 | 3.4 | 68.2 | 4.2 | 70.0 | 15.8 | 76.9 | 2.6 |
| PM70 ECH 50% | 61.5 | 2.8 | 50.6 | 22.3 | 74.3 | 19.4 | 89.2 | 1.6 |
| PM70 ECH fibre | 64.3 | 4.7 | 64.8 | 2.2 | 83.5 | 15.0 | 88.0 | 6.9 |
| PM400 5% | 87.9 | 6.5 | 69.9 | 10.6 | 96.8 | 6.0 | 90.0 | 6.6 |
| DEAE PM70 5% | 70.9 | 0.9 | 76.5 | 9.4 | 75.8 | 9.1 | 82.3 | 0.8 |
| DEAE PM70 ECH 50% | 53.5 | 4.1 | 69.8 | 1.9 | 60.2 | 10.8 | 84.1 | 5.0 |
| CM PM70 5% | 68.5 | 5.9 | 74.2 | 14.3 | 48.9 | 10.9 | 81.3 | 15.2 |
| CM PM70 ECH 50% | 60.9 | 0.8 | 66.9 | 9.4 | 69.6 | 1.9 | 88.2 | 5.4 |
| Blood ref | 100.0 | 5.7 | 100.0 | 10.4 | 100.0 | 8.9 | 100.0 | 9.4 |

The absorbance at 280 nm was measured prior to CRP analysis for calculation of protein recovery.

DBS samples were analysed as single samples and blood references in duplicates in the CRP ELISA assay and A280 measurement.

Leptin ELISA

The Human Leptin ELISA Kit was used according to manufacturer's instruction except dilution recommendations (serum to be diluted 1:3 in buffer supplied with kit). Since spiked sample another dilution need to be used and three dilutions were tested in a pre-study (1:50, 1:800 and 1:4000). 1:800 was chosen since the reference and sample ended up in the linear part of the standard curve. DBS samples were analysed as single samples and blood references in duplicates.

β2GP1 ELISA

The Human β2GP1 ELISA Kit was used according to manufacturer's instruction except dilution recommendations (serum to be diluted 1:5000). Three dilutions were tested in Soaked prototypes gave as in the previous studies higher recovery of CRP. Ficoll of higher molecular size, PM70 and PM400 gave 25% higher CRP recovery for paper soaked with PM400 after storage one week at 37° C. Covalently modified paper shows best effect if the Ficoll was attached directly to the paper fibres. This may be due to higher degree of modification.

Some positive effect on recovery of leptin was found by the papers soaked with higher Mw Ficoll, although the uncertainty was higher in this ELISA, with standard deviations ranging from 2 to 22% within the triplicate results.

The standard deviation was large also in the β2GP1 assay (up to 27%). Ficoll PM400 gave higher recovery than the reference paper after storage at 37° C. indicating a stabilizing effect of this media.

ELISA assays for three proteins have been used for evaluation of stability during the DBS workflow. A high recovery has been assumed to reflect good stability during the interpretation of the result. However, depending on the antibody used in the assay even partially degraded and denatured proteins may contribute to the overall result and this has not been possible to control for. All ELISA kits used in the study were aimed for serum samples.

Detailed evaluation of DBS recovery was difficult to obtain due to generally high standard deviation in the ELISA assays. Many steps are involved in the DBS workflow compared to doing the assay from serum samples.

To summarize the result it can be concluded that paper soaked with Ficoll PM400 is beneficial for certain proteins upon storage as DBS.

Soaked Ficoll PM400 was almost as good as untreated paper for β2GP1 and beneficial for both CRP and β2GP1 during storage at elevated temperature with less decrease in recovery compared to other prototypes.

Example 5—Stability of Alkaline Phosphatase in Dried Blood Spots

Alkaline phosphatase (ALP) catalyzes the hydrolysis of phosphate esters in an alkaline environment. In this study the ALP activity was measured with substrate p-Nitrophenyl phosphate (pNPP). One product of the reaction, p-nitrophenol, exhibits yellow colour under alkaline conditions (maximal absorbance at 405 nm). The rate of the reaction is directly proportional to the enzyme activity.

ALP activity was measured for prototypes with DBS stored at 37° C. for a week

Blood sample spiked with 20 µg/ml ALP: 15 µl of spiked blood are spotted on papers. Let the solutions air dry for at least 2 hours. One set of all 12 prototype paper with DBS was stored at −20° C. and the other set at 37° C. for one week. 2 spots were made for each prototype and temperature.

After storage, the papers were let settle at room temperature. The spots were punched out as 10 mm discs using a steel cork borer, hammer and a plastic cutting board. The disc was placed in a 10 mL well of a Uniplate, and 400 µL of the elution PBS-T buffer (PBS with 0.05% Tween 20) added. The plate was put on a shaker at 500 rpm for 1 hour, stored in refrigerator overnight and on a shaker again for 1 hour. For ALP activity measurements, 5 µl of the extracted solution were mixed with 195 µl of substrate pNPP solution and its absorbance at 405 nm was followed.

TABLE 6

ALP activity recovery of extracted solutions from the prototypes.

| Paper | Concentration in soaking/coupling solution (wt %) | ALP activity recovery (%) |
| --- | --- | --- |
| Plain 31ETF paper (reference) | — | 88 |
| Handsheet from repulped 31ETF | — | 85 |
| 31ETF soaked w DEAE Ficoll PM70 | 5 | 83 |
| 31ETF soaked w CM Ficoll PM70 | 5 | 104 |
| 31ETF soaked w Ficoll PM20 | 5 | 85 |
| 31ETF soaked w Ficoll PM70 | 5 | 89 |
| 31ETF soaked w Ficoll PM400 | 5 | 98 |
| 31ETF with ECH-coupled Ficoll PM20 | 50 | 107 |
| 31ETF with ECH-coupled Ficoll PM70 | 50 | 99 |
| 31ETF with ECH-coupled DEAE Ficoll PM70 | 50 | 96 |
| 31ETF with ECH-coupled CM Ficoll PM70 | 50 | 92 |
| Handsheet from repulped 31ETF, with ECH-coupled Ficoll PM70 | 50 | 95 |

Best results on the ALP analysis were seen when using prototypes where Ficoll molecules were covalently coupled, the activity after storage at +37° C. looks good for these prototypes, but also for the paper soaked with Ficoll PM400. These results indicate that the enzyme activity is good even after storage of the blood spotted papers at +37° C. for one week.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for preserving a biological sample, the method comprising:
   a) providing a paper having a surface weight of 40-800 g/m$^2$, the paper comprising cellulose fibers or glass fibers, and further comprising 4-30 percentage by weight ("wt %") of a hydrophilic branched carbohydrate polymer in the paper wherein the carbohydrate polymer is covalently bound to the cellulose fibers or glass fibers, and wherein water extractables in the paper are 0.1-25 wt %;
   b) applying the biological sample on the paper and forming a sample spot with the applied sample absorbed on the paper; and
   c) drying the paper with the applied sample absorbed thereon, thereby preserving the biological sample.

2. The method of claim 1, wherein the biological sample is a whole blood sample.

3. The method of claim 1, further comprising storing the dried paper for at least one week.

4. The method of claim 1, wherein the paper comprises 10-25 wt % of the carbohydrate polymer.

5. The method of claim 1, wherein a residual moisture content of the dried sample paper is less than 10%.

6. The method of claim 1, wherein water extractables in the paper are 0.1-5 wt %.

7. The method of claim 1, wherein the water extractables in the paper are 3-20 wt %.

8. The method of claim 1, wherein the carbohydrate polymer has an average molecular weight of about 70-400 kDa.

9. The method of claim 1, wherein a 10 wt % water solution of the carbohydrate polymer has a viscosity of 1-10 mPas at 20° C.

10. The method of claim 1, wherein the carbohydrate polymer is a polysucrose.

11. The method of claim 1, further comprising storing the dried paper and extracting the biological sample from the dried paper after storage, the extracted biological sample further comprising a protein preserved in a biologically active state.

12. The method of claim 11, wherein the protein is a storage-sensitive protein.

13. The method of claim 11, further comprising recovering the protein in the biologically active state with a recovery of at least 60%.

14. The method of claim 1, further comprising storing the dried paper at a storage temperature of at least 0° C.

15. The method of claim 14, wherein the storage temperature is 0-40° C.

16. The method of claim 1, wherein the paper further comprises 5-300 micromole/g negatively or positively charged groups, wherein the negatively or positively charged groups are covalently bound to at least one of the cellulose fibers, the glass fibers, or the carbohydrate polymer.

17. The method of claim 16, wherein the negatively charged group is a carboxylate group.

18. The method of claim 16, wherein the positively charged group is an amine group.

19. A method for preserving a biological sample, the method comprising:
   a) providing a paper comprising cellulose fibers or glass fibers, and further comprising 4-30 percentage by weight ("wt %") of a hydrophilic branched carbohydrate polymer in the paper wherein the carbohydrate polymer is covalently bound to the cellulose fibers or glass fibers, the carbohydrate polymer is a polysucrose, and water extractables in the paper are 0.1-25 wt %;
   b) applying the biological sample on the paper and forming a sample spot with the applied sample absorbed on the paper; and
   c) drying the paper with the applied sample absorbed thereon, thereby preserving the biological sample.

* * * * *